(12) United States Patent
van Aller et al.

(10) Patent No.: US 9,421,161 B2
(45) Date of Patent: Aug. 23, 2016

(54) HERBAL COMPOSITION AND A METHOD OF MAKING THEREOF

(76) Inventors: Robert Thomas van Aller, Hattiesburg, MS (US); Geoffrey Thomas van Aller, Ocean Springs, MS (US); Robert Merrick van Aller, Pearlington, MS (US)

( * ) Notice: Subject to any disclaimer, the term of this patent is extended or adjusted under 35 U.S.C. 154(b) by 1171 days.

(21) Appl. No.: 13/443,572

(22) Filed: Apr. 10, 2012

(65) Prior Publication Data

US 2013/0266671 A1 Oct. 10, 2013

(51) Int. Cl.
- *A61K 36/38* (2006.01)
- *A61K 8/97* (2006.01)
- *A61Q 19/06* (2006.01)

(52) U.S. Cl.
CPC .................. *A61K 8/97* (2013.01); *A61K 36/38* (2013.01); *A61Q 19/06* (2013.01)

(58) Field of Classification Search
CPC ...................................................... A61K 36/38
USPC ........................................................ 424/730
See application file for complete search history.

(56) References Cited

U.S. PATENT DOCUMENTS

| | | |
|---|---|---|
| 6,291,241 B1 | 9/2001 | Castor et al. |
| 6,699,512 B2 | 3/2004 | Quintanilla Almagro et al. |
| 2003/0207940 A1 * | 11/2003 | Shan ...................... A61K 31/12 514/544 |
| 2007/0122492 A1 | 5/2007 | Behr et al. |
| 2008/0241101 A1 | 10/2008 | Amano et al. |

FOREIGN PATENT DOCUMENTS

KR 20120058830 6/2012

OTHER PUBLICATIONS

Foster et al. A Field Guide to Medicinal Plants and Herbs of Eastern and Central North America. Houghton Mifflin Company.2000, p. 105, In5 from bottom; p. 106, In20 from bottom.

* cited by examiner

*Primary Examiner* — Chris R Tate
(74) *Attorney, Agent, or Firm* — Keaty Law Firm LLC

(57) ABSTRACT

A topical composition is prepared using macerated leaves of St. Andrew's Cross (*hypericum hypericoides*). An aqueous extract of the leaves is mixed with ethanol to form a spray or to saturate a wet wipe and administer to a mammal skin for treatment a variety of skin conditions, including eczema, psoriasis, rosacea, cellulitis, contact dermatitis, seborrhoeic dermatitis, nummular dermatitis, dandruff, stasis dermatitis, perioral dermatitis, dermatitis herpetiformis, ecthyma, impetigo, shingles, urticaria, tinea pedis, tinea manuum, tinea cruris, sunburn, insect bites and stings, jellyfish stings, granuloma annulare, bullous pemphigoid, lichen planus, bed sore, inflammations caused by waterborne vectors, diaper rash, heat rash, pityriasis rosea, jungle rot, scleroderma, skin rashes and photo-aging.

10 Claims, No Drawings

HERBAL COMPOSITION AND A METHOD OF MAKING THEREOF

BACKGROUND OF THE INVENTION

This invention relates to an herbal composition containing *Hypericum hypericoides* (St. Andrew's Cross) and a method of making thereof. More particularly, the present invention relates to an herbal composition designed for treatment of skin conditions.

The skin is the largest organ of the human body. Skin infections can be either bacterial, viral or fungal in nature. A significant portion of Americans as well as the global population are afflicted with skin conditions including but not limited to eczema, psoriasis, rosacea, cellulitis, contact dermatitis (both irritant and allergic) including poison ivy, poison oak and poison sumac from contact with urushiol (organic allergen), seborrhoeic dermatitis, nummular dermatitis, dandruff, stasis dermatitis, perioral dermatitis, dermatitis herpetiformis, ecthyma, impetigo, shingles, urticaria, tinea pedis (athlete's foot), Tinea Manuum, tinea cruris, sunburn, inflammation from insect bites and stings, inflammation from jellyfish stings, granuloma annulare, bullous pemphigoid, lichen planus, bed sore, inflammation from puncture wounds from catfish and other waterborne creatures, diaper rash, heat rash, pityriasis rosea, jungle rot (trench foot) and scleroderma. Skin rashes, which often go misdiagnosed or undiagnosed, are very common and fall into at least one of the above-mentioned categories of conditions.

Some of these cases can be severe and can result in a rash, itching, bleeding sores, hair loss, permanent scarring and subsequent breakdown of one's immune system and internal organs. Particular types of systemic cases can often cause people to become isolated from the general population due to embarrassment and shame and can have profound psychological and physiological effects on their entire lives. Death can occur as a result of some of these skin problems and is well documented in medical literature all over the world.

Systemic steroids, also called corticosteroids, glucocorticoids or cortisones, are commonly prescribed for the treatment of the above-mentioned skin conditions. These medications are administered orally or by injections. They are synthetic derivatives of the natural steroid, cortisol, which is produced by the adrenal glands. Topical corticosteroids are also used to treat the skin conditions; they are applied directly to the skin. Inhaled steroids are breathed in.

High dose steroids can trigger depression, anxiety, panic, mood swings, fluid retention, increased blood pressure, sleep disturbances, and psychiatric side effects. Weight gain, redistribution of body fat, skin and hair changes, eye changes, musculoskeletal, gastrointestinal, cardiovascular, and immune changes are among other possible side effects.

High doses of systemic corticosteroids such as prednisone are sometimes prescribed for inflammatory diseases, which manifest themselves in the skin. These high doses can cause a condition known as Cushing Syndrome. Symptoms of Cushing Syndrome include easy bruising and purple striae (stretch marks) of the skin over the abdomen, buttocks and thighs, telangiectatic cheeks (broken capillaries), fragile skin and poor wound healing, acne and excessive hair growth in women on their faces, necks, chests, abdomens and thighs. Women may also show clitoral hypertrophy and male-pattern baldness.

Doctors often prescribe topical steroids to patients with the above-mentioned skin conditions. While topical steroids are effective in reducing inflammation, they also have significant side effects. Most of these side effects are seen with long-term use, but some may be noticed within days of starting therapy.

Tachyphylaxis is the tolerance the skin develops to the vasoconstrictive action of topical steroids. After repeated use of topical steroids, the capillaries in the skin do not constrict as well, requiring higher doses or more frequent application of the steroid. With high-potency steroids this effect has been documented after four days of applying a topical steroid three times a day. The ability of the blood vessels to constrict returns about four days after stopping therapy.

Steroid rosacea is a side effect commonly observed in fair-skinned people who already have rosacea. A typical example occurs when a person uses a very mild steroid on the face to counteract the facial flushing. This gives pleasing results, but tolerance develops, causing the person to use a higher strength steroid. At this point any attempt to cut down on the steroid application or stop altogether causes intense facial redness and pustules.

Repeated use of topical steroids in the same area can cause thinning of the epidermis and changes in the connective tissue of the dermis or skin atrophy. The skin becomes lax, wrinkled, and shiny. Affected areas can be depressed below the level of normal skin with visible telangiectasias, hypopigmentation, and prominence of underlying veins. In most cases the atrophy is reversible once topical steroid use is stopped, but it may take months for the skin to "thicken" again.

Repeated use of topical steroids in areas where skin touches skin such as the groin and armpits can result in striae, or stretch marks. Stretch marks from topical steroids are permanent and irreversible. These stretch marks can be very itchy and may require a lower potency steroid to relieve the itching. It is recommended to progressively decrease the steroid potency until topical steroids therapy in these areas can be terminated.

Because topical steroids change the way the immune system functions, they can inhibit the skin's ability to fight off bacterial or fungal infections. A typical example of this is seen when someone applies a topical steroid to an itchy groin rash. If this is a fungal infection, the rash gets redder, itchier, and spreads more extensively than a typical fungal infection. The resulting rash is a bizarre pattern of widespread inflammation with pustules called tinea incognito.

Some people may be allergic to a component of the topical steroid base, or vehicle. Patch-testing of a group of patients with dermatitis revealed that about 4-5% of them were allergic to topical steroids. People who have chronic skin conditions and use multiple prescription or over-the-counter topical steroids are at higher risk of developing allergies to topical steroids.

Glaucoma is a disease in which the pressure inside the eye increases to the point of damaging the optic nerve. There are isolated cases reports of people developing glaucoma after long-term use of topical steroids around the eyes. How topical steroids applied around the eyes cause glaucoma is not completely understood, but it is believed that enough of the steroid can be absorbed and get into the eye.

Topical immunomodulators (TIMs) including brand name products Protopic (Tacrolimus) and Elidel (Pimecrolimus) work by altering the body's immune response to allergens, preventing flare ups of eczema and other skin rashes. In 2005, the FDA warned doctors to prescribe Elidel and Protopic with caution due to concerns over a possible cancer risk associated with their use. The two creams carry the FDA's strongest "black box" warning on their packaging to alert doctors and patients to these potential risks. The warning advises doctors to prescribe short-term use of Elidel and Protopic only after other available eczema treatments have failed in adults and children over the age of two.

Biologics such as Enbrel (Etanercept) and Humira (adalimubab) can be prescribed for severe skin conditions and their prolonged use can lead to pneumonia, cellulitis, septic arthritis, bronchitis, gastroenteritis, pyelonephritis, sepsis, abscess and osteomyelitis, tuberculosis, cancer, congestive heart failure, hepatitis, and a number of other fungal, viral and bacterial infections.

The cause of most skin disorders is unknown. According to some statistics, one percent of the U.S. population dies every year from the overuse of medication or mistreatment of skin disorders using conventional medicine.

There exists therefore a need for a safer treatment of skin disorders, particularly a treatment that avoids the use of harsh medications and the associated serious side effects.

SUMMARY OF THE INVENTION

It is, therefore, an object of the present invention to provide a natural composition that can relieve a variety of skin conditions.

It is another object of the invention to provide a plant-based composition that can relieve serious skin disorders without introducing life-endangering side effects.

It is a further object of the present invention to provide an herbal composition that can be administered topically or aurally to a person suffering from skin disorders.

It is still a further object of the invention to provide a method of making an herbal composition that can be used for treatment of a variety of skin conditions.

It is still a further object of the invention to provide a method of administering an herbal composition in a form of a spray or wet wipes for treatment of skin conditions.

These and other objects of the invention are achieved through a provision of an herbal topical composition, which is prepared using macerated leaves of St. Andrew's Cross (*hypericum hypericoides*). An aqueous extract of the leaves is mixed with a hydroxyl to form a spray or to saturate a wet wipe and topically administer to a mammal skin for treatment a variety of skin conditions. The skin conditions include eczema, psoriasis, rosacea, cellulitis, contact dermatitis, seborrhoeic dermatitis, nummular dermatitis, dandruff, stasis dermatitis, perioral dermatitis, dermatitis herpetiformis, ecthyma, impetigo, shingles, urticaria, tinea pedis, tinea manuum, tinea cruris, sunburn, insect bites and stings, jellyfish stings, granuloma annulare, bullous pemphigoid, lichen planus, bed sore, inflammations caused by waterborne vectors, diaper rash, heat rash, pityriasis rosea, jungle rot, scleroderma, skin rashes and photo-aging.

The aqueous extract is prepared using boiling distilled water, to which the plant material is added, mixture stirred to increase contact with water and then vacuum filtered. The filtered material is then mixed with alcohol and used as a topical agent to treat a variety of skin conditions.

In the preferred embodiment, ethanol is used as a preservative of the extract. Optionally, glycerin can be added.

DETAIL DESCRIPTION OF THE INVENTION

The herbal composition of the present invention is completely natural and does not contain steroids or heavy metals (mercury, lead, etc.), which can be found in conventional creams and ointments used for the treatment of skin disorders. Unlike synthetic drugs and invasive method of treatment, the application of the composition according to the instant invention has no side effects such as irritation of the digestive tract and skin, allergic reactions and pain caused by medications, and unlike other herbal preparations, has a wider range and stronger action.

An aqueous solution of *Hypericum hypericoides*, commonly known as St. Andrew's Cross, has been found to have a remarkably positive effect on the above-mentioned skin conditions, including eczema, psoriasis, rosacea, cellulitis, contact dermatitis (both irritant and allergic) including poison ivy, poison oak and poison sumac from contact with urushiol (organic allergen), seborrhoeic dermatitis, nummular dermatitis, dandruff, stasis dermatitis, perioral dermatitis, dermatitis herpetiformis, ecthyma, impetigo, shingles, urticaria, tinea pedis (athlete's foot), Tinea Manuum, tinea cruris, sunburn, inflammation from insect bites and stings, inflammation from jellyfish stings, granuloma annulare, bullous pemphigoid, lichen planus, bed sores, inflammation from puncture wounds from catfish and other waterborne vectors, diaper rash, heat rash, pityriasis rosea, jungle rot (trench foot), scleroderma, skin rashes and photo-aging.

*Hypericum hypericoides* (L.) Crantz ssp. *Hypericoides* is a perennial flowering shrub native to Southern and Southeastern regions of the United States. It is classified in Dicot group, Clusiaceae family, genus *Hypericum*. It grows 1-3 feet in size, blooming from June to September. Its native habitat is dry woods, pine barrens, sand hills and ridges and floodplains.

Some evidence exists of the root of *Hypericum hypericoides* having been chewed as an antidote to rattlesnake bites. A tea made from the root has been used to relieve colic, fevers, pain and diarrhea. It has been applied externally to ulcerated breasts. A tea made from the leaves has been used for kidney and bladder ailments and skin problems. A milky substance from the plant has been rubbed on sores. This evidence is almost anecdotal. However, the tests conducted by the inventors support the claims that when topically applied, an aqueous extract of the leaves of *hypericum hypericoides* relieves a variety of skin conditions, as will be described in more details hereinafter.

According to the method of the present invention, preparation of the herbal composition consists of several phases:

1. Maceration—maceration is the first step of preparation, where the leaves of St. Andrew's Cross (can be used fresh and dried) are chopped in small pieces. Plants can be chopped and ground in a blender, mixer and chopper grinder.

2. Extraction—Extraction is the second step of preparation where the plant material (macerated leaves) is mixed with boiling distilled water at a rate of 1:25 to 1:30, preferably at a rate of 1:27. This step can be carried out in a glass or Pyrex vessel.

After mixing, the mixture is removed from heat and stirred with a non-metal stirrer every two minutes for about 12-18 minutes. Between the stirring cycles, the vessel is covered with a lid. Stirring increases the contact area of water with the plant material and speeds up the process of forming the final composition. In addition, the dissolution or breakdown of the ingredients that make the basic structure of the leaves creates a series of aromatic alcohols, aldehydes, pentoses, hexoses and tannins in the herbal composition.

3. Filtering—Filtering is the third step of preparation, where the mixture is filtered using a fine vacuum filter. Suspended solids and water are removed at this stage.

4. Preservation—The filtered extract is immediately preserved by mixing it with a stabilizing/preservative agent selected from the hydroxyl group, such as for instance pure alcohol in the form of ethanol or methanol. The stabilizing preserving agent is added at a ratio of between 4-6% by volume of the filtered composition, preferably at a ratio of 3% by volume. The composition of the aqueous extract of *hypericum hypericoides* and alcohol is refrigerated and kept in the refrigerated state at a temperature of about 3-5 degrees Celsius (37.4-41 degrees Fahrenheit).

Example

According to one example, an extract of *hypericum hypericoides* was made to isolate the active components of *hypericum hypericoides* in an aqueous solution. According to the method, about 6 liters (about 1.6 gallons) of distilled water are deposited in a heat-proof container and the water is brought to a boil. Then, about 225 grams (about 0.5 pounds) of macerated plant leaves were deposited in the container of boiling distilled water. The container is then removed from heat. The contents of the container were stirred with a non-metallic rod every two minutes. A lid was placed over the container top to keep it covered while not stirring. The stirring cycle continues for about 16 minutes.

Next, the mixture was forced through a 10 micron vacuum filter to remove suspended solids and as much water from the plant material as possible. The resultant mixture was immediately preserved with 3% of ethyl alcohol by volume and refrigerated to 3.3 Celsius (38 degrees Fahrenheit).

It is noted that the active compounds in the extract are sensitive to the following and should not be contaminated at any point with any of these compounds: acids, surfactants, sodium benzoate, methyl paraben and amphoteric metals. The tests demonstrated that the extract preserved with ethyl alcohol and refrigerated has the durability over one year.

The aqueous extract contains two active compounds and demonstrates the following properties:

1. The extract as tested had a concentration of active compounds of 0.311%-0.362% by weight. The pH was from 6.30 to 6.62.

2. Over time there is some slight settling of very fine particulate matter. This is harmless and can be filtered out if desired.

It was noted that when the plant is extracted in the presence of aluminum, severe precipitation and darkening occurs. As with other flavonoids care should be taken to prevent oxidation. It is preferred that the extract be preserved quickly and remained refrigerated when not used. The extract may be frozen if it is not to be used for an extended period of time. The air space in the storage container(s) should be minimized if not eliminated. Oxygen was noted to shorten the useful life of the product.

The tests showed that glycerin will prevent oxidation of the active compounds at room temperature but does not necessarily prevent bacterial and/or fungal growth. Ethanol acts as a preservative and stabilizer of the active compounds and prevents bacterial and fungal growth if the extraction is refrigerated and any oxygen is kept out of the container.

The following concentrations were also obtained from extractions with the percentages of solids by weight of the two active compounds in the extract:

4.0 grams plant material/100 ml distilled water yielded 0.339% solids by weight 2.0 grams plant material/100 ml distilled water yielded 0.238% solids by weight 1.0 grams plant material/100 ml distilled water yielded 0.138% solids by weight 0.5 grams plant material/100 ml distilled water yielded 0.081% solids by weight The tests demonstrated that these different concentrations are effective for varying degrees of severity of the skin ailments described above. It should also be noted this may vary depending on the time of the year the plant is harvested (warmer months will yield higher concentrations given an equal amount of plant material in a given amount of distilled water). The pH of the extract is slightly acidic due to the phenolic groups of the two active compounds.

Use of Extract as a Topical Agent

The product in the form of a spray has been tested in the following manner to treat the above-mentioned skin condition: it was sprayed on the affected area(s) 3-4 times per day and allowed to air dry on the skin. The tests showed that a small amount may be poured in the hands and rubbed on the affected area(s). A wipe can be saturated with the herbal composition and used to wipe the affected area. Itching or burning in all tested cases ceased immediately or in less than one to two minutes. Rash in the form of bumps or redness, scabs, dryness, sores, etc. cleared up within two-three days.

One particular case tested on a patient suffering from cellulitis took approximately one week to relieve. After the cellulitis returned in a 14 days it was treated again. This happened twice and the herbal composition was topically applied again. In that case, the bacterial infection did not return.

The tests showed that severe cases of eczema and psoriasis may take considerably longer to relieve (1 to 2 weeks depending on the severity of the case). Some cases of eczema and psoriasis did return but often several weeks later and the returning cases were less severe (quite possibly due to the discontinuation of steroid use). These return cases were easily relieved within two or three days of treatment using the herbal composition. It must be noted that some of the tested eczema and psoriasis cases were individuals with a history of long term steroid treatment use, whose immune systems seem took longer to respond to the topical treatment using the extract of this invention.

In another test, the extract in the form of a spray was used to treat sunburn. The relief was instantaneous and there was no subsequent peeling or itching. The redness associated with sunburn disappeared within 24-36 hours.

The extract in the form of a spray was also tested to relieve insect bites and stings including yellow jackets, wasps, gnats, deer flies, etc. The relief was instantaneous.

During tests it was noted that extract helps in the treatment of photo-aging. Topical application of the herbal composition resulted in diminished appearance of wrinkles on the face and other parts of the body.

The herbal composition was also successfully tested to relieve razor burn and an astringent. The extract was topically applied and demonstrated beneficial results almost instantaneously.

Some eczema manifests itself on the lining of the inner ear and is a dermatological concern for professionals. At present, the tinnitus problem has no known cure and all treatments are judged by the user of the treatment. Treatments considered to be the most effective are steroidal and considered marginally effective and then only at the onset of the problem. Some tests were conducted by applying the herbal composition to the subject's ears for treatment of tinnitus (aural administration). While the studies of these problems using the instant herbal composition are ongoing, preliminary results demonstrate subject's positive response to the treatment when the spray was administered directly into the ear cavity.

Preliminary toxicology studies indicate that the extract is not toxic to humans or other mammals. One of the inventors personally consumed four ounces per day of the extract for two months with no noticeable side effects.

The extract prepared according to this invention has been tested on dogs for itching and works remarkably well. It has been tested as a nasal mist to stop the production of mucous on surgical sores in the nasal passages. It has been tested on one case of post operative contact dermatitis which could not be cured with conventional medicine over a period of 8 months. The case was relieved in approximately one week after using this extraction of this invention.

The tests showed that the extract has a potential for treatment of fungal, bacterial and viral infections (athlete's foot, cellulitis and shingles respectively) to a great extent.

The compounds in the extract are flavonoids. It is noted that the flavonoids may modify allergens, viruses and carcinogens acting as biological "response modifiers." The inventors believe that the mode of action of the extract is the interruption of the immune system response which is caused by the complicated reactions of T-Cells and subsequent histamine production by the mast cells. The flavonoids in the extract are believed to bind dermal proteins and other foreign proteins like wasp venom.

Although not empirically confirmed, it is also believed that the mechanism of action of the herbal composition of this invention on mammal skin is associated with interruption of the body immune response for a period long enough for the skin to heal. It was noted that most skin disorders return, except for certain types of contact dermatitis, but they return at a lower frequency and severity and can be kept under control with relative ease.

It is envisioned that the composition provided by this invention can be used as medical cosmetics for treating various diseases and changes of the skin, such as erythema (caused by shaving and make up). Using of composition after shaving, leads to a mild burning and calming the skin. After frequent use of make-up, or due to lack of safety measures, tension and irritation of the skin can occur. During preliminary tests, the composition was applied directly to the face, and the first noticeable signs of the disappearance of itching and rough skin were reported within several hours of application as a spray or saturated wipe.

The inventors were unable to identify any side effects when using this extract in the manner described.

The herbal composition can be used in the form of spray, wet wipes, and directly to the affected areas. Other forms suitable for topical application are envisioned. This composition is formulated to influence several diseases and disorders with active ingredients that have antioxidant, antibacterial, antiviral, antifungal, anti-inflammatory, antiseptic, regenerative, stimulatory, cosmetic and other effects.

The combination of ingredients shows synergistic effect in contact with skin. Unlike other herbal-based compositions, the composition provided by this invention has a greater effect due to the unique extract of *hypericum hypericoides* and ways of applying this composition by spraying with spray or applying directly to skin or using saturated wet wipes which increases the action of active agents because of their uniform application and facilitates penetration into the skin pores.

This invention is a natural herbal composition which is based on an aqueous extract of *hypericum hypericoides* leaves. It contains iron, various tannins, (mostly catehins), essential oils, resins, anthocyans, hypericin—red color, carotene, choline, vitamin C, and some traces of alkaloids. It has a broad antibacterial, antiviral and anti-inflammatory effect. St. Andrew's Cross extract treats inflammatory processes on the skin, superficial wounds and burns by reducing inflammation of the skin.

Many changes and modifications can be made to the composition and method of the present invention without departing from the spirit thereof. We, therefore, pray that our rights to the present invention be limited only by the scope of the appended claims.

We claim:

1. A process for preparing a stabilized/preserved *Hypericum hypericoides* extract comprising:
   macerating *Hypericum hypericoides* plant material;
   mixing the macerated plant material in distilled boiling water for a suitable predetermined period of time to obtain an aqueous extract;
   forcing the aqueous extract through a vacuum filter to obtain a filtered extract;
   adding a hydroxyl stabilizing/preservative agent to the filtered extract at a ratio of 4-6% by volume of the hydroxyl stabilizing/preservative agent to the filtered extract to obtain said stabilized/preserved *Hypericum hypericoides* extract, wherein said stabilized/preserved *Hypericum hypericoides* extract has a pH of between 6.30 and 6.62.

2. The process of claim 1, wherein the plant material comprises *Hypericum hypericoides* leaves.

3. The process of claim 1, wherein the plant material is mixed with the distilled boiling water at a ratio of 1:25 to 1:30.

4. The process of claim 1, wherein the hydroxyl stabilizing/preservative agent is an alcohol.

5. The process of claim 1, wherein the hydroxyl stabilizing/preservative agent is added to the filtered extract at a ratio of 3% by volume of the hydroxyl stabilizing/preservative agent to the filtered extract.

6. The process of claim 1, wherein the hydroxyl stabilizing/preservative agent is ethanol.

7. The process of claim 1, further comprising refrigerating said stabilized/preserved *Hypericum hypericoides* extract.

8. The process of claim 1, wherein the concentration of active compounds in said stabilized/preserved *Hypericum hypericoides* extract is between 0.311% and 3.62% by weight.

9. The process of claim 2, wherein the *Hypericum hypericoides* leaves are macerated, and wherein the macerated leaves are mixed with the distilled boiling water at a ratio of 1:25 to 1:30.

10. The process of claim 1, wherein the stabilized/preserved *Hypericum hypericoides* extract is added to a topical composition in an amount effective for topically treating skin conditions selected from the group consisting of eczema, psoriasis, rosacea, cellulitis, contact dermatitis, seborrhoeic dermatitis, nummular dermatitis, dandruff, stasis dermatitis, perioral dermatitis, dermatitis herpetiformis, ecthyma, impetigo, shingles, urticaria, tinea pedis, tinea manuum, tinea cruris, sunburn, insect bites and stings, jellyfish stings, granuloma annulare, bullous pemphigoid, lichen planus, bed sore, inflammations caused by waterborne vectors, diaper rash, heat rash, pityriasis rosea, jungle rot, scleroderma, and skin rashes.

* * * * *